US009033935B2

(12) United States Patent
Boström

(10) Patent No.: US 9,033,935 B2
(45) Date of Patent: May 19, 2015

(54) MEDICAMENT DELIVERY DEVICE

(75) Inventor: Anders Boström, Ekerö (SE)

(73) Assignee: SHL Group AB, Nacka Strand (SE)

( * ) Notice: Subject to any disclaimer, the term of this patent is extended or adjusted under 35 U.S.C. 154(b) by 324 days.

(21) Appl. No.: 13/499,070

(22) PCT Filed: Sep. 3, 2010

(86) PCT No.: PCT/SE2010/050940
§ 371 (c)(1),
(2), (4) Date: Mar. 29, 2012

(87) PCT Pub. No.: WO2011/040861
PCT Pub. Date: Apr. 7, 2011

(65) Prior Publication Data
US 2012/0184918 A1    Jul. 19, 2012

(30) Foreign Application Priority Data

Sep. 30, 2009  (SE) ...................... 0950710

(51) Int. Cl.
*A61M 5/32*    (2006.01)
*A61M 5/315*   (2006.01)
*A61M 5/20*    (2006.01)
(Continued)

(52) U.S. Cl.
CPC .......... *A61M 5/31501* (2013.01); *A61M 5/2033* (2013.01); *A61M 5/3257* (2013.01); *A61M 5/46* (2013.01); *A61M 2005/3143* (2013.01); *A61M 5/3204* (2013.01)

(58) Field of Classification Search
CPC ............ A61M 5/3202; A61M 5/2033; A61M 5/31501; A61M 5/3257; A61M 2005/3143; A61M 5/008; A61M 5/20; A61M 5/46
USPC .................. 604/110, 163, 192–198, 263, 137
See application file for complete search history.

(56) References Cited

U.S. PATENT DOCUMENTS 6,270,479 B1    8/2001  Bergens et al.
6,544,234 B1 *  4/2003  Gabriel .......................... 604/207
(Continued)

FOREIGN PATENT DOCUMENTS

WO    2006/129196 A1    12/2006
WO    WO2008113198  *    9/2008  .............. A61M 5/20
WO    2009/081103 A1    7/2009

OTHER PUBLICATIONS

Swedish Patent Office, Int'l Search Report in PCT/SE2010/050940, Jan. 3, 2011.
(Continued)

*Primary Examiner* — Bhisma Mehta
*Assistant Examiner* — Hamza Darb
(74) *Attorney, Agent, or Firm* — Piedmont Intellectual Property

(57) ABSTRACT

A medicament delivery device has a housing and a sleeve; a shield within and protruding from the housing; a container having a delivery member, a chamber containing a medicament, and a piston; a drive mechanism having a spring and a plunger rod in contact with the piston; and a container holder having a first locking device releasably connected to a corresponding locking device on the sleeve for holding the holder in an initial state against the drive mechanism and a second locking device surrounded by the sleeve and releasably connected to a corresponding locking device on the plunger rod for protecting the piston from force from the drive mechanism until the holder has moved a certain predetermined distance. The shield releases the first locking device when the shield is pressed against a medicament delivery site, whereby the drive mechanism forces the holder the certain predetermined distance.

20 Claims, 4 Drawing Sheets

(51) Int. Cl.
*A61M 5/46* (2006.01)
*A61M 5/31* (2006.01)

(56) References Cited

U.S. PATENT DOCUMENTS 7,442,185 B2 * 10/2008 Amark et al. ................ 604/137

2007/0073232 A1 3/2007 Pickhard
2010/0137801 A1 * 6/2010 Streit et al. .................... 604/138

OTHER PUBLICATIONS

Swedish Patent Office, Written Opinion in PCT/SE2010/050940, Jan. 3, 2011.

* cited by examiner

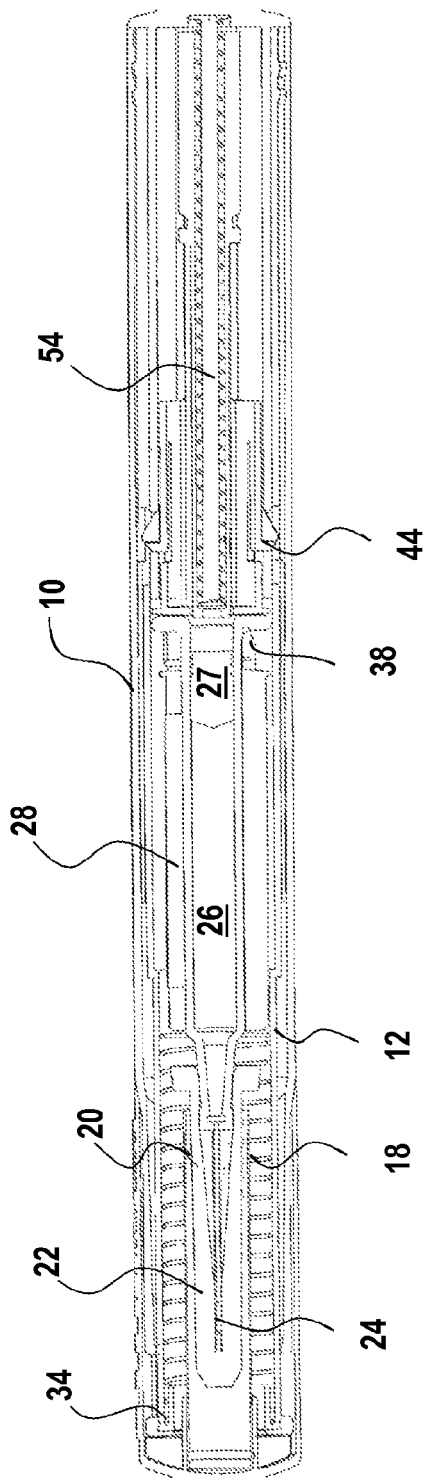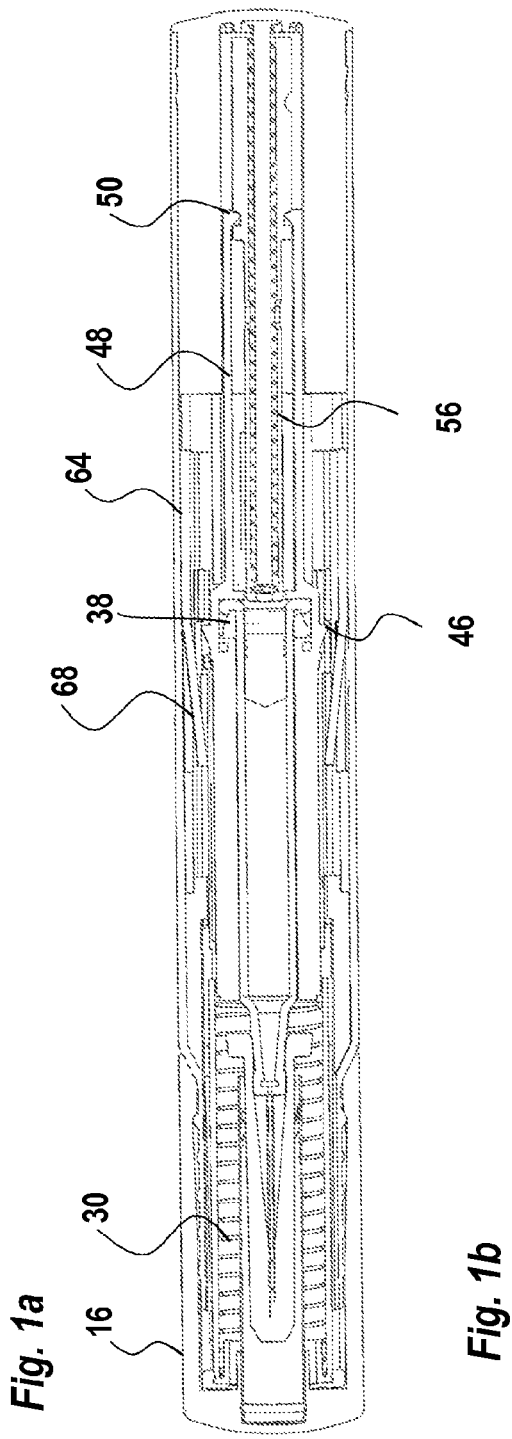
Fig. 1a
Fig. 1b

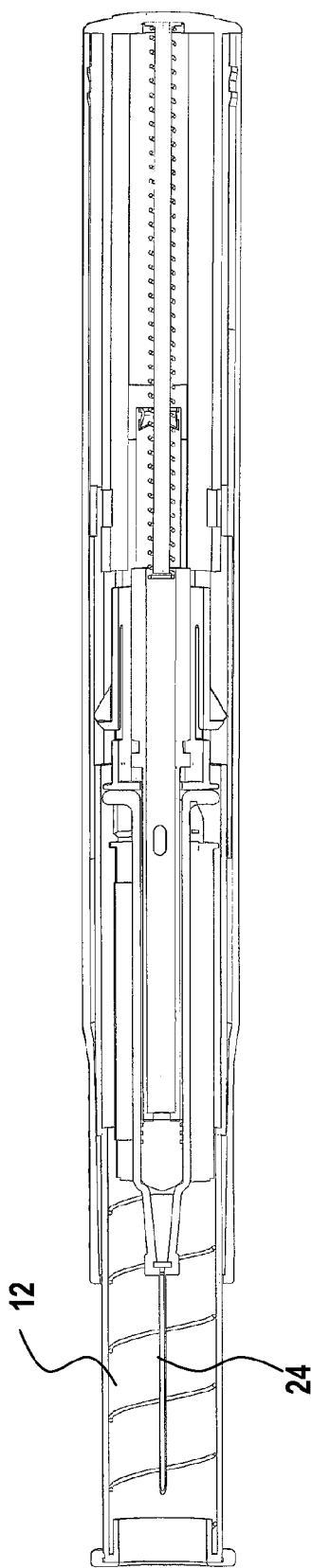
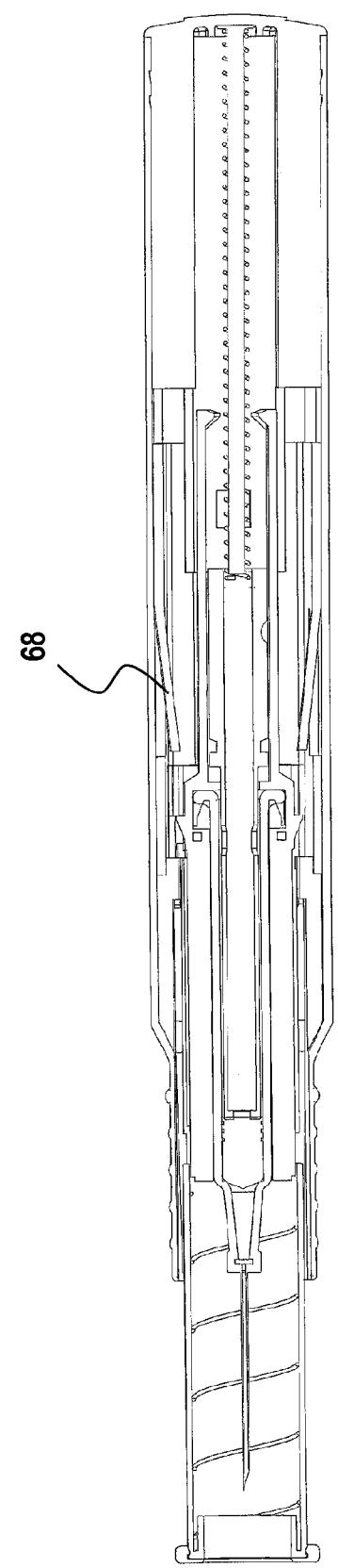
Fig. 4a
Fig. 4b

MEDICAMENT DELIVERY DEVICE

TECHNICAL AREA

The present invention relates to a medicament container holder arranged to be used in a medicament delivery device and in particular a medicament container holder that is capable of preventing injuries due to broken medicament containers.

TECHNICAL BACKGROUND

There are a number of medicament delivery devices on the market in which a medicament container is placed, usually in an appropriate container holder designed to accommodate the medicament container.

Many medicament delivery devices are arranged with a number of automatically triggered functions such as penetration, injection, withdrawal, protection of a medicament delivery member after delivery, just to mention a few.

Many of these functions require a number of components, making the device rather complex, as well as require handling aspects that may be difficult for some users, even though the functions as such are automatic. There are also aspects regarding the interaction between different components requiring handling tolerance chains that may be quite complex when a number of components are to interact.

It is thus in many devices a desire to keep the number of components as low as possible in order to reduce the complexity of the functions as well as reducing the tolerance chains. Also in view of handling and administration of medicament the number of components of the device should be kept as low as possible in order to provide a clear and concise operation.

Further, according to the type of drug and the ailment which the medicament is designed to alleviate, every medicament should have a most appropriate injection depth to achieve high efficacy. Therefore, any leakage of medicament before a needle tip arrive the expected injection depth might lose the expected efficacy. Therefore it is desirable that the injection does not start already during penetration, which otherwise often is the case when one spring, acting on a plunger rod, performs both penetration and injection. On the other hand it is often necessary to use two springs when first a penetration is performed followed by an injection.

There is thus room for further improvements in the technical area of medicament delivery devices with a certain amount of automatically performed functions.

BRIEF DESCRIPTION OF THE INVENTION

A main aim of the present invention is to remedy the shortcomings and drawbacks of the state of the art medicament delivery devices.

This aim is obtained by a medicament delivery device having the features of the independent patent claim. Preferable embodiments of the invention form the subject of the dependent patent claims.

According to a main aspect of the invention, it is characterised by medicament delivery device comprising a generally tubular housing having opposite proximal and distal ends, wherein the housing is provided with a coaxial tubular sleeve extending from its distal end towards the proximal end; a generally tubular medicament delivery member shield coaxially and slidably arranged within the housing, wherein a proximal portion of the tubular medicament delivery member shield protrudes from the proximal end of the housing; a medicament container provided with a medicament delivery member, a chamber containing a medicament, and an axial movable piston; drive means comprising a plunger rod having opposite proximal and distal ends, and a force spring means, wherein the proximal end of the plunger rod is in contact with the piston; wherein the device further comprises a medicament container holder coaxially arranged to the drive means and capable of supporting the medicament container; wherein the medicament container holder comprises a first locking means releasibly connected to corresponding locking means on the coaxial tubular sleeve forming a first locking engagement for holding the medicament container holder in an initial state against a force from the drive means, wherein the medicament delivery member shield is capable of releasing said first locking engagement when the medicament delivery member shield is pressed against a medicament delivery site, whereby said drive means forces said medicament container holder a certain predetermined distance towards the proximal end of the device; and a second locking means surrounded by the coaxial tubular sleeve and releasibly connected to corresponding locking means on the plunger rod forming a second locking engagement for preventing the piston to be affected by the force from the drive means until said medicament container holder has moved the certain predetermined distance.

According to another aspect of the invention, the first locking means comprises outwardly extending ledges arranged on flexible arms on the outer surface of the medicament container holder, and wherein the corresponding locking means are openings on the proximal surface of the coaxial tubular sleeve having mutual shape as that of the ledges so that the ledges fit into the openings.

According to still another aspect of the invention, the second locking means comprises distally extending and flexible tongues having inwardly directed ledges, wherein the corresponding locking means is a circumferential groove on the plunger rod having a mutual shape as that of the ledges so that the ledges fit into the groove.

According to yet another aspect of the invention, when the medicament container holder is in the initial state, the plunger rod is held against the force from the drive means by the inwardly directed ledges of the tongues fitted into the groove of the plunger rod, and by the coaxial tubular sleeve which surrounds and prevents the tongues from flexing radially outwards.

According to a further aspect of the invention, the second locking engagement is released after the first locking engagement is released and when the second locking means reaches the proximal end of the coaxial tubular sleeve.

According to still a further aspect of the invention, the medicament container holder further comprises a first stop means arranged to cooperate with a corresponding stop means on the inner surface of the housing when the medicament container holder is moved towards the proximal end of the device.

According to yet a further aspect of the invention, the device further comprises a medicament delivery member shield force spring means arranged between a proximal end wall of the medicament container holder and an annular recess at the proximal end of the medicament delivery member shield for pushing said medicament delivery member shield towards the proximal end of the device when the medicament delivery member shield is removed from the medicament delivery site.

According to another aspect of the invention, the device further comprises medicament delivery member shield locking means arranged to the inner surface of the housing for cooperating with the distal annular surface of the medicament delivery member shield after the medicament delivery member shield has been pushed towards the proximal end of the device and thereby preventing the medicament delivery member shield to be moved towards the distal end of the device.

According to still another aspect of the invention, the device further comprises medicament delivery member shield locking means arranged on a lock sleeve which is coaxially and fixedly arranged inside the housing and which is coaxially surrounding the medicament container holder.

According to yet another aspect of the invention, the medicament container holder further comprises a second stop means arranged to cooperate with corresponding stop means on the medicament delivery member shield.

According to a further aspect of the invention, the device further comprises a dampening member arranged to the medicament container holder and capable of dampening forces that are exerted on said medicament container when the medicament container holder is released from its initial state.

According to still a further aspect of the invention, the dampening member is capable of pressing a distal surface of said medicament container against a proximally directed surface of said medicament container holder.

There are a number of benefits with the present invention. Due to the design of the medicament container holder having both first and second locking means, it is possible to use only one spring means for both a penetration and subsequent injection. This greatly reduces the number of components compared to the conventional devices.

This further enables a very compact device with short tolerance chains, which ensures a reliable functionality of the different components providing the functions. A further advantage is that the device is activated by merely pressing it against the medicament delivery site, whereby first a penetration is activated, without affecting the medicament in the medicament container, and then when the penetration has been performed to the requested penetration depth, then an injection is activated. It is thus ensured that the injection only takes place when the injection needle has reached its full depth.

Further, in order to ascertain reduced risk of breaking the medicament container during activation, the dampening means reduces the forces on the medicament container. Further, the use of the dampening means enables the medicament container to be positioned such that a reference surface of the medicament container, the distal end surface, is positioned against a wall fixed on the medicament container, which enables a good control of tolerance chains of the device.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which FIGS. 1a, b show cross-sectional views of a medicament delivery device according to the present invention.

DETAILED DESCRIPTION OF THE INVENTION

In the present application, when the term "distal part/end" is used, this refers to the part/end of the medicament delivery device, or the parts/ends of the members thereof, which under use of the medicament delivery device is located the furthest away from the medicament delivery site of the patient. Correspondingly, when the term "proximal part/end" is used, this refers to the part/end of the medicament delivery device, or the parts/ends of the members thereof, which under use of the injection device is located closest to the medicament delivery site of the patient.

Figure 2:
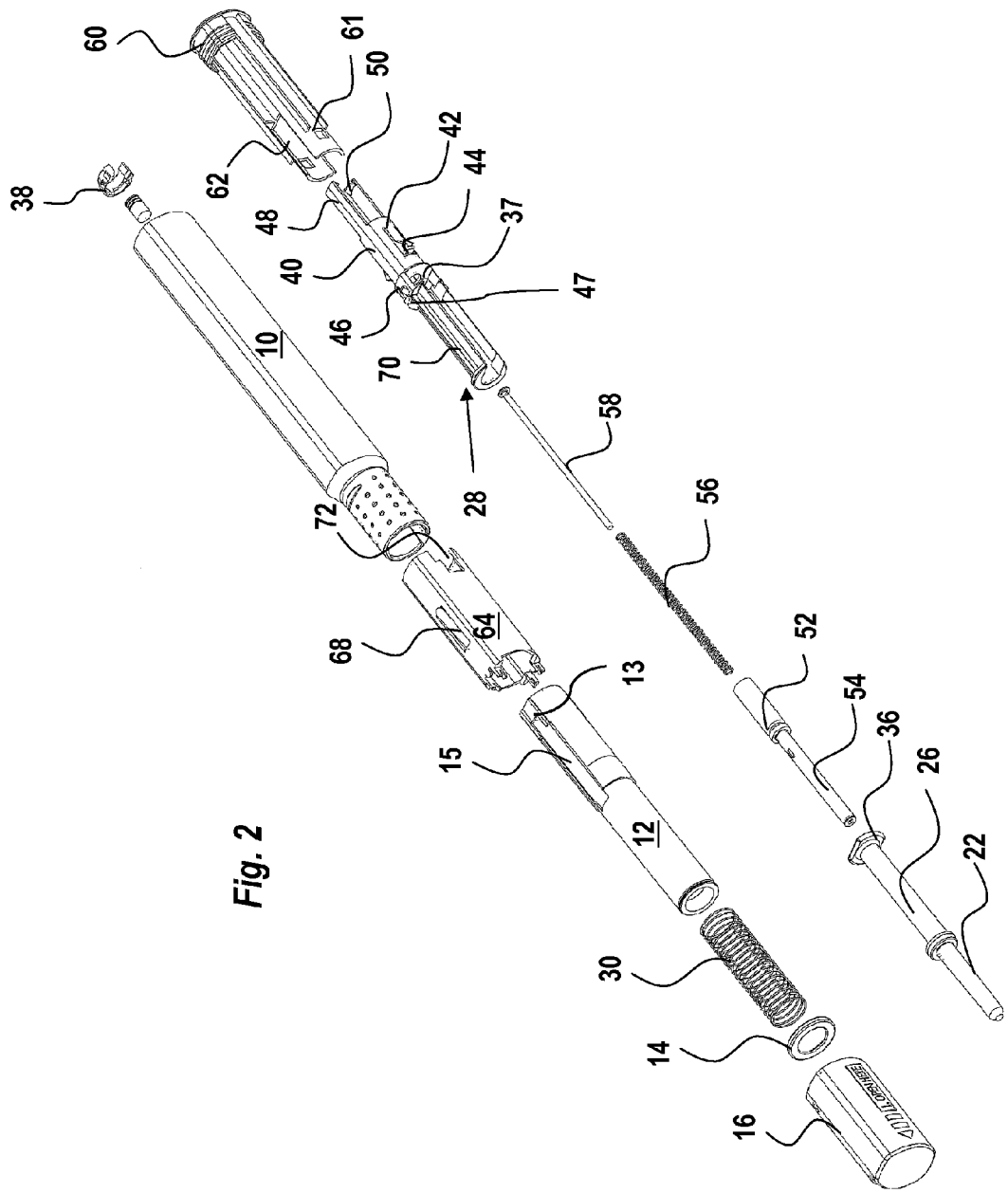
FIG. 2 shows an exploded view of the medicament delivery device of FIG. 1, FIGS. 3a, b show cross-sectional views of the medicament delivery device of FIG. 1 after a medicament delivery member has been moved into a medicament delivery site, and FIGS. 4a, b show cross-sectional views of the medicament delivery device of FIG. 1 after a medicament delivery has been performed.

A medicament delivery device in the present invention, FIG. 2, comprises:
- a generally tubular housing 10 having opposite proximal and distal ends, wherein the housing is provided with a coaxial tubular sleeve 60 extending from its distal end towards the proximal end;
- a generally tubular medicament delivery member shield 12 coaxially and slidably arranged within the housing 10, wherein a proximal portion of the tubular medicament delivery member shield protrudes from the proximal end of the housing 10;
- a medicament container 26, such as e.g. a syringe, provided with a medicament delivery member 24, such as e.g. an injection needle, a chamber containing a medicament, and an axial movable piston 27;
- drive means comprising a plunger rod 54 having opposite proximal and distal ends, and a force spring means 56, wherein the proximal end of the plunger rod is in contact with the piston 27;
- a medicament container holder 28 coaxially arranged to the drive means and capable of supporting the medicament container 26; and
- a releasable cover 16 coaxially arranged on the distal circumferential surface of the housing 10.

The proximal end of the medicament delivery member shield is arranged with a ring-shaped member 14, FIG. 2, the distal circumferential area of the medicament delivery member shield is arranged with rectangular openings 15, FIG. 2, and the cover 16 is arranged with a coaxial sleeve-like member 18 which comprises inwardly projecting hooks 20 arranged to engage a resilient sheath 22, wherein said sheath 22 is surrounding the medicament delivery member, FIG. 1a.

The medicament container holder 28, which is arranged slidable inside said housing, is further arranged with a distally directed extension, comprising a first tubular part 40. The tubular part is provided with a first locking means 42, 44 releasibly connected to corresponding locking means 61 on the coaxial tubular sleeve 60 forming a first locking engagement for holding the medicament container holder in an initial state against a force from the drive means 54, 56 wherein the medicament delivery member shield 12 is capable of releasing said first locking engagement when the medicament delivery member shield 12 is pressed against a medicament delivery site, whereby said drive means 54, 56 forces said medicament container holder 28 a certain predetermined distance towards the proximal end of the device.

The extension then transforms into two distally directed second locking means 48, 50 surrounded by the coaxial tubular sleeve 60. The second locking means are releasibly connected to corresponding locking means 52 on the plunger rod 54 forming a second locking engagement for preventing the piston 27 such as e.g. a rubber stopper to be affected by the force from the drive means until said medicament container holder 28 has moved the certain predetermined distance.

The first locking means comprises outwardly extending ledges 44 arranged on flexible arms 42 on the outer surface of the medicament container holder 28, and wherein the corresponding locking means are openings 61 on the proximal surface of the coaxial tubular sleeve 60 having mutual shape as that of the ledges 44 so that the ledges 44 fit into the openings 61.

The second locking means comprises distally extending flexible tongues 48 having inwardly directed ledges 50, wherein the corresponding locking means is a circumferential groove 52 on the plunger rod having a mutual shape as that of the ledges 50 so that the ledges fit into the groove 52.

The medicament container holder 28 further comprises a first stop means 47 and a second stop means 46 on the tubular part 40. The first stop means 47 is/are arranged to cooperate with a corresponding stop means 11 on the inner surface of the housing when the medicament container holder is moved towards the proximal end of the device; and the second stop means 46 is/are arranged to cooperate with corresponding stop means 13 on the medicament delivery member shield 12.

The plunger rod 54 is further hollow and inside it the force spring means 56 is arranged, such as a compression spring. The compression spring 56 is positioned and cocked between an inner proximal and transversal end wall of the plunger rod 54 and an inner distal and transversal end wall of the coaxial tubular sleeve 60. Inside the compression spring 56 a guide rod 58 is arranged. When the medicament container holder is in the initial state, the inwardly directed ledges 50 of the flexible tongues 48 of the medicament container holder 28 are held in position in the groove 52 by the inner surface of the coaxial tubular sleeve 60, preventing the tongues 48 from flexing radially outwards and thereby holding the plunger rod against the force from the cocked compression spring. The coaxial tubular sleeve 60 is further provided with cut-outs 62 in its proximal area. Further, the coaxial tubular sleeve 60 is either part of the housing or is a separate part which is attached to the distal end of the housing 10.

The device further comprises a medicament delivery member shield force spring means 30 arranged between a proximal end wall 32 of the medicament container holder and an annular recess 34 at the proximal end of the medicament delivery member shield 12 for pushing said medicament delivery member shield towards the proximal end of the device when the medicament delivery member shield is removed from the medicament delivery site.

The device also comprises medicament delivery member shield locking means 68 arranged to the inner surface of the housing 10 for cooperating with the distal annular surface of the medicament delivery member shield after the medicament delivery member shield has been pushed towards the proximal end of the device and thereby preventing the medicament delivery member shield to be moved towards the distal end of the device. It is also conceivable that the medicament delivery member shield locking means 68 are arranged on a lock sleeve 64 which is coaxially and fixedly arranged inside the housing 10 and which is coaxially surrounding the medicament container holder 28.

As seen in FIG. 2, the medicament delivery member shield locking means 68 are flexible and protruding inclined inwardly proximally directed arms, arranged on the side surface of the lock sleeve 64. The arms 68 are in contact with longitudinal ridges 70 on the proximal part of the medicament container holder 28 through the rectangular openings 15 of the medicament delivery member shield 12. The distal end of the lock sleeve 64 is arranged with cut-outs 72. The distal end of the medicament container 26 is arranged with radially outwardly directed flanges 36, which flanges are seated in cut-outs 37 in the side wall of the container holder 28.

The device also comprises a dampening member 38 arranged to the medicament container holder 28 and capable of dampening forces that are exerted on said medicament container 26 when the medicament container holder is released from its initial state. The dampening member 38 is U-shaped and is capable of pressing a distal surface of said medicament container against a proximally directed surface of said medicament container holder 26. This arrangement facilitates the handling of tolerance chains of the device since the distal end surface of the medicament container is well documented by the manufacturers of such containers and thus can be seen as a reference surface.

The device is intended to function as follows. When the device is delivered to a user, a medicament container 26 is positioned in the medicament holder and the medicament container holder is positioned within the housing. The medicament delivery member 24 is covered by both the protective sheath 22 as well as the protection cover 16. The medicament container holder 28 is held in place by the outwardly extending ledges 44 of the arms 42 fitting into the openings 61 on the proximal area of the coaxial tubular sleeve 60. Further the plunger rod 54 is held in position against the force of the compression spring 56 by the inwardly directed ledges 50 of the flexible tongues 48 of the medicament holder 28, which tongues 48 are in engagement with the groove 52 of the plunger rod. Thus the medicament container holder is in the initial state and ready for use. The medicament delivery member shield 12 is prevented from moving in the proximal direction against the force of the medicament delivery member shield spring 30 by the second stop means 46 on the tubular part 40 which is wedge-like protrusion in contact with the corresponding stop means 13 which is a distal side surface of the rectangular opening 15 of the medicament delivery member shield 12.

Figure 3A:
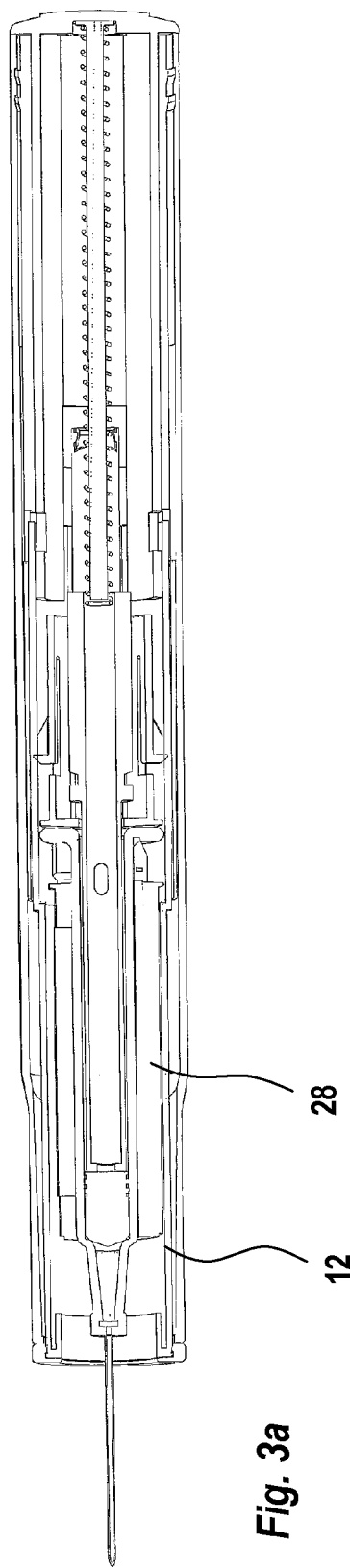
Figure 3B:
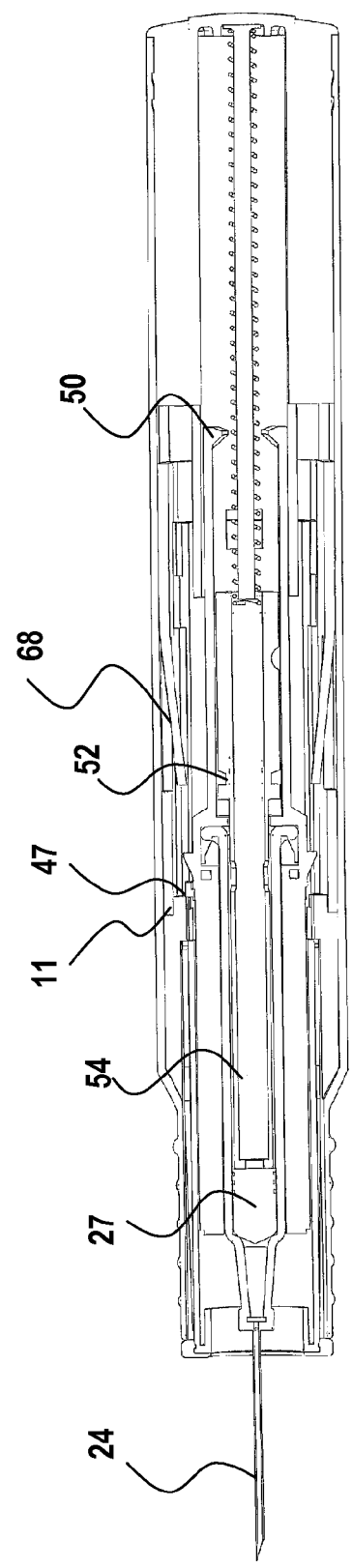

When a medicament delivery is to be performed, the proximal end of the medicament delivery member shield is pressed against a medicament delivery site. The medicament delivery member shield 12 is then pushed into the housing 10 with a movement in the distal direction whereby the distal end of the medicament delivery member shield 12 comes in contact with proximally directed inclined surfaces of the outwardly extending ledges 44 of the arms 42 of the medicament container holder 28. This contact causes the arms 42 of the medicament holder 28 to move radially inwards whereby the outwardly extending ledges 44 move out of contact with the side surfaces of the openings 61. The medicament container holder 28 is now free to move and is pushed a certain predetermined towards the proximal end of the device by force of the compression spring 56 acting between the inner proximal and transversal end wall of the plunger rod 54 and the inner distal and transversal end wall of the coaxial tubular sleeve 60. The plunger rod 54 is however still fixed in relation to the medicament container holder 28 due to the connection of the inwardly directed ledges 50 inside the circumferential groove 52. The movement of the medicament container holder 28 towards the proximal end of the device causes the medicament delivery member to move into the medicament delivery site, e.g. causing a penetration of an injection needle 24 into an injection site. At the same time the medicament delivery member shield spring 30 is compressed, FIG. 3. The movement of the medicament container holder 28, i.e. the penetration, is stopped by the first stop means 47 which is a ledge on the medicament container holder coming in contact with the corresponding stop means which is a ledge 11 on the inner surface of the housing. Due to the dampening member the risk of breaking the medicament container is reduced when the movement of the medicament container holder 28, i.e. the penetration, is stopped.

When now the medicament container holder 28 has moved certain predetermined distance towards the proximal end of the device and the penetration is stopped, the ends of the tongues 48 of the medicament container holder 28 reach the cut-outs 62 in the proximal end of the coaxial tubular sleeve 60. The tongues 48 are now free to move outwardly in the radial direction and will release the plunger rod 54.

The plunger rod 54 is forced in the proximal direction by the force of the compression spring 56, urging the stopper 27 in the proximal direction, thereby performing a delivery of the medicament through the medicament delivery member 24. The movement of the medicament container holder 28 towards the proximal end of the device causes the medicament delivery member shield locking means 68 to pass over second stop means 46 of the medicament container holder 28.

When the medicament delivery now has been performed and the device is removed from the medicament delivery site, the medicament delivery member shield 12 is free to move in the proximal direction by the force of the compressed medicament delivery member shield spring 30. The medicament delivery member shield 12 thus surrounds the medicament delivery member 24 and is prevented from being moved back in the distal direction by the medicament delivery member shield locking means 68 which cooperate with the distal annular surface of the medicament delivery member shield, thereby avoiding accidental needle sticks, FIG. 4. The device may now be discarded.

It is to be understood that the embodiments described above and shown in the drawings only are to be regarded as non-limiting examples of the invention and that it may be modified in many ways within the scope of the patent claims.

The invention claimed is:

1. A medicament delivery device, comprising:
a generally tubular housing having opposite proximal and distal ends and a coaxial tubular sleeve extending from the distal end toward the proximal end;
a generally tubular medicament delivery member shield coaxially and slidably arranged within the housing, wherein a proximal portion of the tubular medicament delivery member shield protrudes from the proximal end of the housing;
a medicament container, including a medicament delivery member, a chamber containing a medicament, and an axially movable piston;
a drive mechanism, including a plunger rod having opposite proximal and distal ends, and a force spring device, wherein the proximal end of the plunger rod is in contact with the piston; and
a medicament container holder coaxially arranged to the drive mechanism, configured for supporting the medicament container, and including:
a first locking device releasably connected to a corresponding locking device on the coaxial tubular sleeve forming a first locking engagement for holding the medicament container holder in an initial state against a force from the drive mechanism, wherein the medicament delivery member shield is configured for releasing the first locking engagement when the medicament delivery member shield is pressed against a medicament delivery site, whereby the drive mechanism forces the medicament container holder a certain predetermined distance toward the proximal end of the device; and
a second locking device surrounded by the coaxial tubular sleeve and releasably connected to a corresponding locking device on the plunger rod forming a second locking engagement for preventing the piston from being affected by force from the drive mechanism until the medicament container holder has moved the certain predetermined distance.

2. The medicament delivery device of claim 1, wherein the first locking device includes outwardly extending ledges arranged on flexible arms on an outer surface of the medicament container holder, and the corresponding locking device includes openings on a proximal surface of the coaxial tubular sleeve having shapes corresponding to the ledges so that the ledges fit into the openings.

3. The medicament delivery device of claim 2, wherein the second locking device includes distally extending and flexible tongues having inwardly directed ledges, and the corresponding locking device is a circumferential groove on the plunger rod having a shape corresponding to the ledges so that the ledges fit into the groove.

4. The medicament delivery device of claim 3, wherein the medicament container holder further includes a first stop device configured for cooperating with a corresponding stop device on the inner surface of the housing when the medicament container holder is moved toward the proximal end of the device.

5. The medicament delivery device of claim 4, further comprising a medicament delivery member shield force spring device arranged between a proximal end wall of the medicament container holder and an annular recess at the proximal end of the medicament delivery member shield for pushing the medicament delivery member shield toward the proximal end of the device when the medicament delivery member shield is removed from the medicament delivery site.

6. The medicament delivery device of claim 5, further comprising a medicament delivery member shield locking device arranged to the inner surface of the housing for cooperating with the distal annular surface of the medicament delivery member shield after the medicament delivery member shield has been pushed toward the proximal end of the device and thereby preventing the medicament delivery member shield from moving toward the distal end of the device.

7. The medicament delivery device of claim 6, further comprising a medicament delivery member shield locking device arranged on a lock sleeve coaxially and fixedly arranged inside the housing and coaxially surrounding the medicament container holder.

8. The medicament delivery device of claim 7, wherein the medicament container holder further includes a second stop device configured for cooperating with a corresponding stop device on the medicament delivery member shield.

9. The medicament delivery device of claim 8, further comprising a damping member arranged to the medicament container holder and configured for damping forces exerted on the medicament container when the medicament container holder is released from its initial state.

10. The medicament delivery device of claim 9, wherein the damping member is configured for pressing a distal surface of the medicament container against a proximally directed surface of the medicament container holder.

11. The medicament delivery device of claim 1, wherein the second locking device includes distally extending and flexible tongues having inwardly directed ledges, and the corresponding locking device is a circumferential groove on the plunger rod having a shape corresponding to the ledges so that the ledges fit into the groove.

12. The medicament delivery device of claim 11, wherein in the initial state the plunger rod is held against the force from the drive mechanism by the inwardly directed ledges of the tongues fitted into the groove of the plunger rod, and by the coaxial tubular sleeve surrounding and preventing the tongues from flexing radially outward.

13. The medicament delivery device of claim 1, wherein the second locking engagement is released after the first locking engagement is released and when the second locking device reaches the proximal end of the coaxial tubular sleeve.

14. The medicament delivery device of claim 1, wherein the medicament container holder further includes a first stop device configured for cooperating with a corresponding stop device on the inner surface of the housing when the medicament container holder is moved toward the proximal end of the device.

15. The medicament delivery device of claim 1, further comprising a medicament delivery member shield force spring device arranged between a proximal end wall of the medicament container holder and an annular recess at the proximal end of the medicament delivery member shield for pushing the medicament delivery member shield toward the proximal end of the device when the medicament delivery member shield is removed from the medicament delivery site.

16. The medicament delivery device of claim 15, further comprising a medicament delivery member shield locking device arranged to the inner surface of the housing for cooperating with the distal annular surface of the medicament delivery member shield after the medicament delivery member shield has been pushed toward the proximal end of the device and thereby preventing the medicament delivery member shield from moving toward the distal end of the device.

17. The medicament delivery device of claim 16, further comprising a medicament delivery member shield locking device arranged on a lock sleeve coaxially and fixedly arranged inside the housing and coaxially surrounding the medicament container holder.

18. The medicament delivery device of claim 15, wherein the medicament container holder further includes a second stop device configured for cooperating with a corresponding stop device on the medicament delivery member shield.

19. The medicament delivery device of claim 15, further comprising a damping member arranged to the medicament container holder and configured for damping forces exerted on the medicament container when the medicament container holder is released from its initial state.

20. The medicament delivery device of claim 19, wherein the damping member is configured for pressing a distal surface of the medicament container against a proximally directed surface of the medicament container holder.

* * * * *